United States Patent
Groat et al.

(12)

(10) Patent No.: US 6,458,528 B1
(45) Date of Patent: Oct. 1, 2002

(54) DIAGNOSIS OF FELINE IMMUNODEFICIENCY VIRUS INFECTION USING ENV/GAG POLYPEPTIDE MARKERS

(75) Inventors: Randall G. Groat, Falmouth; Thomas P. O'Connor, Westbrook; Brion Mermer, Cumberland, all of ME (US)

(73) Assignee: Idexx Laboratories, Inc., ME (US)

( * ) Notice: Subject to any disclaimer, the term of this patent is extended or adjusted under 35 U.S.C. 154(b) by 0 days.

(21) Appl. No.: 09/089,878

(22) Filed: Jun. 3, 1998

Related U.S. Application Data

(60) Provisional application No. 60/085,615, filed on May 15, 1998.

(51) Int. Cl.[7] .................................................. C12Q 1/70
(52) U.S. Cl. ............................ 435/5; 435/7.1; 435/7.9; 435/7.91; 435/7.92; 435/7.93; 435/7.94; 435/7.95; 435/975; 436/518; 436/531; 530/326; 530/327; 530/328; 530/826
(58) Field of Search .............................. 435/5, 7.1, 7.9, 435/7.91, 7.92, 7.93, 7.94, 7.95, 975; 436/518, 531; 530/326–328, 826

(56) References Cited

U.S. PATENT DOCUMENTS

| | | | |
|---|---|---|---|
| 4,016,143 A | * | 4/1977 | Schuurs et al. ........ 195/103.5 R |
| 4,514,505 A | | 4/1985 | Canfield et al. |
| 4,591,552 A | * | 5/1986 | Neurath ......................... 435/7 |
| 4,743,678 A | | 5/1988 | Essex et al. |
| 4,939,096 A | | 7/1990 | Tonelli |
| 4,965,187 A | | 10/1990 | Tonelli |
| 5,037,753 A | | 8/1991 | Pedersen et al. |
| 5,118,602 A | | 6/1992 | Pedersen et al. |
| 5,177,014 A | | 1/1993 | O'Connor et al. |
| 5,219,725 A | | 6/1993 | O'Connor et al. |
| 5,275,813 A | | 1/1994 | Yamamoto et al. |
| 5,356,785 A | | 10/1994 | McMahon et al. |
| 5,413,927 A | | 5/1995 | Tompkins et al. |
| 5,510,106 A | | 4/1996 | Yamamoto et al. |
| 5,565,319 A | | 10/1996 | Pedersen et al. |
| 5,591,572 A | | 1/1997 | Kemp et al. |
| 5,656,732 A | | 8/1997 | Andersen et al. |
| 5,700,655 A | | 12/1997 | Croteau et al. |
| 5,726,010 A | | 3/1998 | Clark |
| 5,726,013 A | | 3/1998 | Clark |

FOREIGN PATENT DOCUMENTS

| | | | |
|---|---|---|---|
| EP | 0 902 286 A2 | | 3/1999 |
| WO | WO 90/06510 | | 6/1990 |
| WO | 92/22573 | * | 12/1992 |
| WO | 97/07817 | * | 3/1997 |

OTHER PUBLICATIONS

Odell et al. *Principles of Competitive Protein–Binding Assays*. N.Y., John Wiley & Sons, 1983, pp. 244–246. QP519.R3P7.*

Voller, "The Enzyme Linked Immunosorbent Assay (ELISA)", published by Microbiological Associates, 2 Diagnostics Horizons, vol. 2, No. 1, Feb. 1978.

O'Connor, Thomas et al., "Characterization of the Major Structured Proteins of Feline T–Lymphotropic Lentivirus (FTLV)", *J. Clin. Micro.*, p. 213, Mar. 1989.

UC Clip Sheet, "Feline Retrovirus Provides Model for Aids Research", Mar. 17, 1987.

Sparger, Ellen, "Feline T–lymptotrophic Lentivirus Infection", Feline Medicine IV; Veterinary Learning Systems, pp. 9–14, 1988.

Ackley, Christopher D. et al., "Immunologic Abnormalities in Pathogen–Free Cats Experimentally Infected with Feline Immunodeficiency Virus", *J. Virol.*, vol. 64, No. 11, Nov. 1990.

Braun, Michael J. et al., "Molecular Cloning of Biologically Active Proviruses of Bovine Immunodeficiency–like Virus", *Virology*, 167:515–523, 1988.

Bryant, Martin L. et al., "Immunodeficiency in Rhesus Monkeys Associated with Original Mason–Pfizer Monkey Virus", *JNCL*, vol. 77, No. 4, Oct. 1986.

Devare, Sushilkumar G. et al., "Biochemical and Immunological Characterization of the Major Envelope Glycoprotein of Bovine Leukemia Virus" *J. Virol.*, vol. 23, No. 2, Aug. 1977.

Dubois–Dalcq, Monique et al., "Assembly of Enveloped RNA Viruses—Assembly of Retroviridae", Springer–Verlag, Wien New York, pp. 149–170.

Egberink, Herman F. et al., "Intracellular proteins of feline immunodeficiency virus and their antigenic relationship with equine infectious anaemia virus proteins", *J. Virol.*, 71:739–743, 1990.

Essex, M. et al., "Antibodies to Cell Membrane Antigens Associated with Human T–Cell Leukemia Virus in Patients with AIDS", *Science*, vol. 220, May 1983.

Fine, Donald L. et al., "Functionally Conserved Determinants on gp70s of Endogenous Primate Retroviruses", *Virol.*, vol. 101, No. 1, Feb. 1980.

Groat, R. et al., "Simultaneous Detection of Antibodies to ENV and GAG Proteins in FIV Diagnostics".

Harbour, D. A. et al., "Isolation of a T–lymphotropic lentivirus from a persistently leucopenic domestic cat", *The Veterinary Record*, 122:84–86, 1988.

Hardy, William D., "Feline T–Lymphotropic Lentiviruses: Retrovirus—Induced Immunosuppression in Cats", *Jour. of Am. Animal Hospital Assoc.*, vol. 24, pp. 241–243, 1988.

(List continued on next page.)

*Primary Examiner*—Jeffrey Stucker
(74) *Attorney, Agent, or Firm*—Fish & Richardson P.C.

(57) ABSTRACT

Methods for determining whether a feline is infected with feline immunodeficiency virus ("FIV"). The methods involve the use of an antibody-binding composition that includes two enhanced polypeptides, one containing an immunogenic fragment of the FIV gag precursor p55 and the other containing an immunogenic fragment of the FIV env precursor gp130. Also featured are devices for practicing these methods.

28 Claims, 3 Drawing Sheets

OTHER PUBLICATIONS

Hellstrom, Karl Erik et al., "Monoclonal Anti–melanoma Antibodies and Their Possible Clinical Use", *Monoclonal Antibodies for Cancer Detection and Therapy*, pp. 19–51, 1985.

Hoppe, J. et al., "Preparation of Biologically Active Platelet– Derived Growth Factor Type BB from a Fusion Protein Expressed in Escherichia coli", *Biochemistry*, vol. 28, No. 7, 1989.

Hosie, Margaret J. et al., "Serological responses of cats to feline immunodeficiency virus", *AIDS*, vol. 4, No. 3, 1990.

Lerner, Richard A., "Tapping the immunological repertoire to produce antibodies of predetermined specificity", *Nature*, 299:592–596, Oct. 1982.

Lombardi, Stefania et al., "Detection of B Epitopes on the p24 gage Protein of Feline Immunodeficiency Virus by Monoclonal Antibodies", *AIDS*, vol. 9, No. 2, 1993.

Lombardi, Stefania et al., "Epitope mapping of the V3 domain of feline immunodeficiency virus envelope glycoprotein by monoclonal antibodies", *J. Virol.*, 76:1893–1899, 1995.

Lutz, H. et al., Monoclonal Antibodies to Three Epitopic Regions of Feline Leukemia Virus p27 and their use in Enzyme–Linked Immunosorbent Assay of p27, *J. Immun. Methods*, 56:209–220, 1983.

Matsudaira, Paul, "Sequence from Picomole Quantities of Proteins Electroblotted onto Polyvinylidene Di–fluoride Membranes", *J. Biol. Chem.*, vol. 262, No. 21, 1987.

Mermer, B. et al., "A recombinant–based feline immunodeficiency virus antibody enzyme–linked immunosorbent assay", *Vet. Immun. and Immunopathology*, 35:133–141, 1992.

Mermer, B. et al., "Similarities Between the Transmembrane Proteins of FIV and HIV", Abstract.

O'Connor, Thomas P., Jr. et al. "Development and Evaluation of Immunoassay for Detection of Antibodies to the Feline T–Lymphotropic Lentivirus (Feline Immunodeficiency Virus)", *J. Clin. Micro.*, 27:474–479, 1989.

Olmsted et al., "Molecular cloning of feline immunodeficiency virus", *Proc. Nat'l Acad. Sci. USA*, 86:2448–2452, 1989.

Olmsted et al., "Nucleotide sequence analysis of feline immunodeficiency virus: Genome organization and relationship to other lentiviruses", *Proc. Nat'l. Acad. Sci. USA*, 86:8088–8092, Oct. 1989.

Parodi, A. L. et al., "Histopathological Changes in Lymph Nodes of Cats Experimentally Infected with the Feline Immunodeficiency Virus (FIV)", *J. Comp. Path.*, 111:165–174, 1994.

Pedersen, N. C. et al., "Implications of the isolation of FTLV", The Veterinary Record, 122:4, Jan. 23, 1988.

Pedersen, Niels et al., "Isolation of a T–Lymphotropic Virus from Domestic Cats with an Immunodeficiency Like Syndrome", 235 *Science* 790, 1987.

Podell, Michael et al., "Progressive Encephalopathy Associated with CD4/CD8 Inversion in Adult FIV–Infected Cats", *J. Acqud. Imm. Def. Syn.*, 15:332–340, 1997.

Pyle, Stephan W. et al., "Purification of 120,000 Dalton Envelope Glycoprotein from Cultural Fluids of Human Immunodeficiency Virus (HIV)—Infected H9 Cells", *AIDS*, 3:387–400, 1987.

Robey et al., "Characterization of Envelope and Core Structural Gene Products of HTLV–III with Sera from AIDS Patients", *Science*, 228:593–595, May 1985.

Robey et al., "Prospect for prevention of human immunodeficiency virus infection: Purified 120–dka envelope glycoprotein induces neutralizing antibody", *Proc. Natl. Acad. Sci. USA*, 83:7023–7027, 1986.

Shaw, George M. et al., "Molecular Characterization of Human T–Cell Leukemia (Lymphotropic) Virus Type III in the Acquired Immune Deficiency Syndrome", *Science*, 226:1165 Dec. 1984.

Siebelink, Kees H. J. et al., "Feline Immunodeficiency Virus (FIV) Infection in the Cat as a Model for HIV Infection in Man: FIV–Induced Impairment of Immune Function", *AIDS*, 6:1373–1378, 1990.

Steinman, Robin et al., "Biochemical and immunological characterization of the major structural proteins of feline immunodeficiency virus", *J. Gen. Virol.*, 71:701–706, 1990.

Talbott, Randy L. et al., "Nucleotide sequence and genomic organization of feline immunodeficiency virus", *Proc. Natl. Acad. Sci. USA*, 86:5743–5747, 1989.

Tilton, Garrett K. et al., "Immunoassay for Detection of Feline Immunodeficiency Virus Core Antigen", *J. Clin. Micro.*, 28:898–904, 1990.

Wingender, Edgar et al., "Expression of Human Parathyroid Hormone in Escherichia coli", *J. Biol. Chem.*, 264:4367–4373, 1989.

Wilson, Barbara M. et al., "Recent Developments in the Periodate Method of Conjugating Horseradish Peroxidase (HRPO) to Antibodies", North Holland Biomedical Press, pp. 215–223, 1978.

Yamamoto, Janet K. et al., "Pathogenesis of experimentally induced feline immunodeficiency virus infection in cats", *Am J. Vet Res.*, 49:1246–1258, Aug. 1988.

* cited by examiner

DIAGNOSIS OF FELINE IMMUNODEFICIENCY VIRUS INFECTION USING ENV/GAG POLYPEPTIDE MARKERS

CROSS REFERENCE TO RELATED APPLICATIONS

Under 35 USC §119(e)(1), this application claims the benefit of prior U.S. provisional application Ser. No. 60/085,615, filed May 15, 1998.

FIELD OF THE INVENTION

This invention is in the general field of diagnosing feline immunodeficiency virus ("FIV") infection.

BACKGROUND OF THE INVENTION

Infection with a variety of lentiviruses is associated with immunodeficiency disease. Cats infected with FIV (Pedersen et al., Science 235:790–793, 1987; U.S. Pat. No. 5,037,753), for example, show a number of pathogenic symptoms reminiscent of acquired immunodeficiency disease ("AIDS") (Yamamoto et al., Am. J. Vet. Res. 49:1246–1258, 1988; Ackley et al., J. Virol. 64:5652–5655, 1990; Siebelink et al., AIDS Res. Hum. Retroviruses 6:1373–1378, 1990). FIV-associated feline AIDS is an important feline disease, with incidences as high as 15% in populations of sick animals (O'Connor et al., J. Clin. Microbiol. 27:474–479, 1989). The transient, low level viremia often seen in connection with the persistence of intracellular proviruses makes detection of the antibody response to infection a reliable assay for infection by FIV.

Enzyme-linked immunosorbent assays ("ELISA") for detecting FIV antibodies use purified, inactivated FIV virions and/or antigens as solid-phase reagents to bind FIV antibodies in samples. Antibodies recognizing epitopes on the gag-encoded p24 capsid ("p24") and p15 nucleocapsid proteins and on the env-encoded gp40 transmembrane ("gp40") and gp100 surface proteins have been detected by radioimmunoprecipitation analysis ("RIPA") or immunoblot (Hosie et al., AIDS 4:215–220, 1990; Steinman et al., J. Gen. Virol. 71:701–706, 1990; Andersen et al., U.S. Pat. No. 5,656,732; Kemp et al., U.S. Pat. No. 5,591,572; Mermer et al., Similarities between the Transmembrane Proteins of FIV and HIV, Cold Spring Harbor Symposium, RNA Tumor Viruses, 1991; Tilton et al., J. Clin. Microbiol. 28:898–904, 1990). Various anti-FIV antibodies have also been generated (O'Connor et al., U.S. Pat. Nos. 5,219,725 and 5,177,014).

IDEXX Laboratories, Inc. markets a FIV diagnostic device under the trademark SNAP® COMBO, which detects FIV antibodies in feline samples. The device includes recombinant p24 as a solid-phase capture reagent. FIV antibody captured by the solid-phase reagent is detected with disrupted FIV conjugated to horseradish peroxidase. See U.S. Pat. Nos. 5,726,010 and 5,726,013.

SUMMARY OF THE INVENTION

Applicants have discovered that detection of FIV antibodies indicative of FIV infection is improved by using a polypeptide marker composition that is enhanced for the presence of both FIV env polypeptides and FIV gag polypeptides. By "enhanced" is meant that the FIV env and gag polypeptides are present in the marker composition at higher weight percentage levels than in a simple mixture of FIV proteins obtained from disrupted virus. Enhancement can be achieved, e.g., by spiking the viral mixture with a purified or partially purified preparation of the env and gag polypeptides, or by using such a preparation as a marker composition without inclusion of the viral mixture.

Accordingly, the invention features a diagnostic method for determining FIV infection by contacting a feline sample (e.g., a serum or blood sample) with an antibody-binding capture composition that includes both enhanced FIV env and gag polypeptides. An enhanced (e.g., purified) polypeptide can be a recombinant or synthetic polypeptide, or a polypeptide isolated from FIV virions. The reaction of antibodies in the sample with the capture composition indicates that the donor of the sample is infected with FIV.

An immunogenic fragment of a polypeptide is a polypeptide fragment that can bind to one or more antibodies that are specific to the polypeptide in its native conformation. Immunogenic fragments of a FIV gag precursor p55 include, but are not limited to, p55 itself, p55 cleavage products such as p24, p15, and p10, and any p55 fragments recognized by monoclonal antibody ("mAb") 2D4 (American Type Culture Collection ("ATCC") HB9890), 3H8 (ATCC HB12531), 4F2 (ATCC HB9888), 2H4 (ATCC HB12530), or 6E6 (ATCC HB9899). Immunogenic fragments of a FIV env precursor gp130 include, but are not limited to, gp130 itself, gp130 cleavage products such as gp40 and gp110; they also include any gp130 fragments containing a cysteine loop of gp40 and any gp130 fragments that bind to mAb 2F11 (ATCC HB10295), 1C9 (ATCC HB12529), or 3H9 (ATCC HB12528). An exemplary immunogenic fragment of gp130 is ELGCNQNQFFCK (SEQ ID NO:1). An exemplary second capture polypeptide is CELGCNQNQFFCK (SEQ ID NO:2).

In one embodiment of the above-described method, the binding composition is attached to a phase (e.g., a solid phase) immiscible with the sample. An antibody-binding detection composition can be applied to detect reaction of antibodies in the feline sample with the capture composition. This detection composition may include two detection polypeptides that respectively contain immunogenic fragments of p55 and gp130. For instance, the detection composition can contain disrupted FIV (e.g., a mixture of viral proteins obtained by disrupting native FIV virions with a detergent) spiked with a peptide having the sequence of SEQ ID NO:1 or 2. The polypeptides in the detection composition are preferably labeled with a detectable moiety, such as an enzyme that catalyzes a detectable reaction, colloidal gold, a radionuclide, and a fluorophore.

Also embraced by the invention is a device for performing an assay that determines whether a feline is infected with FIV. This device contains the above-described antibody-binding capture and detection compositions. In one embodiment, the detection composition is held in a container.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting.

Other features and advantages of the invention will be apparent from the following detailed description, and from the claims.

DETAILED DESCRIPTION

Figure 1:
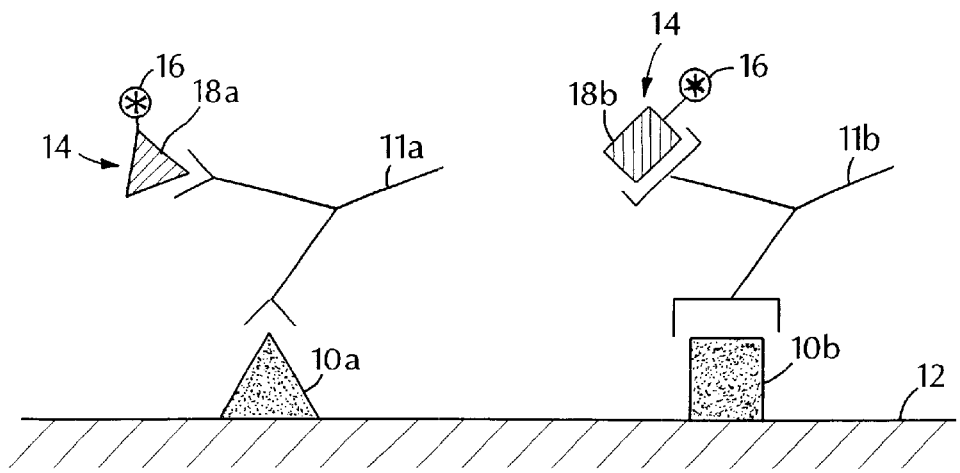
FIG. 1 is a diagram representing the components of a FIV assay of the invention.

The invention features immunoassays for detecting FIV antibodies in a sample. FIG. 1 shows the basic components of one such assay. Antibody is captured by capture reagents (i.e., an antibody-binding composition) 10a and 10b which are immobilized on a solid substrate 12 by any of a large number of known methods. Specifically, the capture reagents are a mixture of FIV polypeptides which may include (a) recombinant p24 as described in greater detail below; and (b) a synthetic env (e.g. gp40) immunodominant peptide ("IDP"), also described below. The capture reagents bind to FIV antibodies 11a and 11b in the sample, and unbound material is washed off or removed by other known means. The presence of captured FIV antibody is detected by the use of a labeled detection reagent 14 that specifically binds to the captured antibody. The reagent is a mixture of native, recombinant, and/or synthetic polypeptides that specifically bind the target antibody. These polypeptides (e.g., 18a and 18b) are each conjugated to an enzyme 16 that catalyzes a detection reaction. Since antibodies are bivalent, the captured FIV antibodies can be detected using the same epitopes as were used in the capture reagents. One specific detection reagent includes disrupted native FIV spiked with a synthetic gp40 IDP that can be the same one as described above.

Any of a large number of known immunoassay formats may be used to detect the presence of anti-FIV antibodies in a sample using the above reagents. One such format is the reverse flow format used in the SNAP® device of IDEXX Laboratories, Inc. and generally disclosed in U.S. Pat. Nos. 5,726,010 and 5,726,013, which are hereby incorporated by reference.

Figure 2:
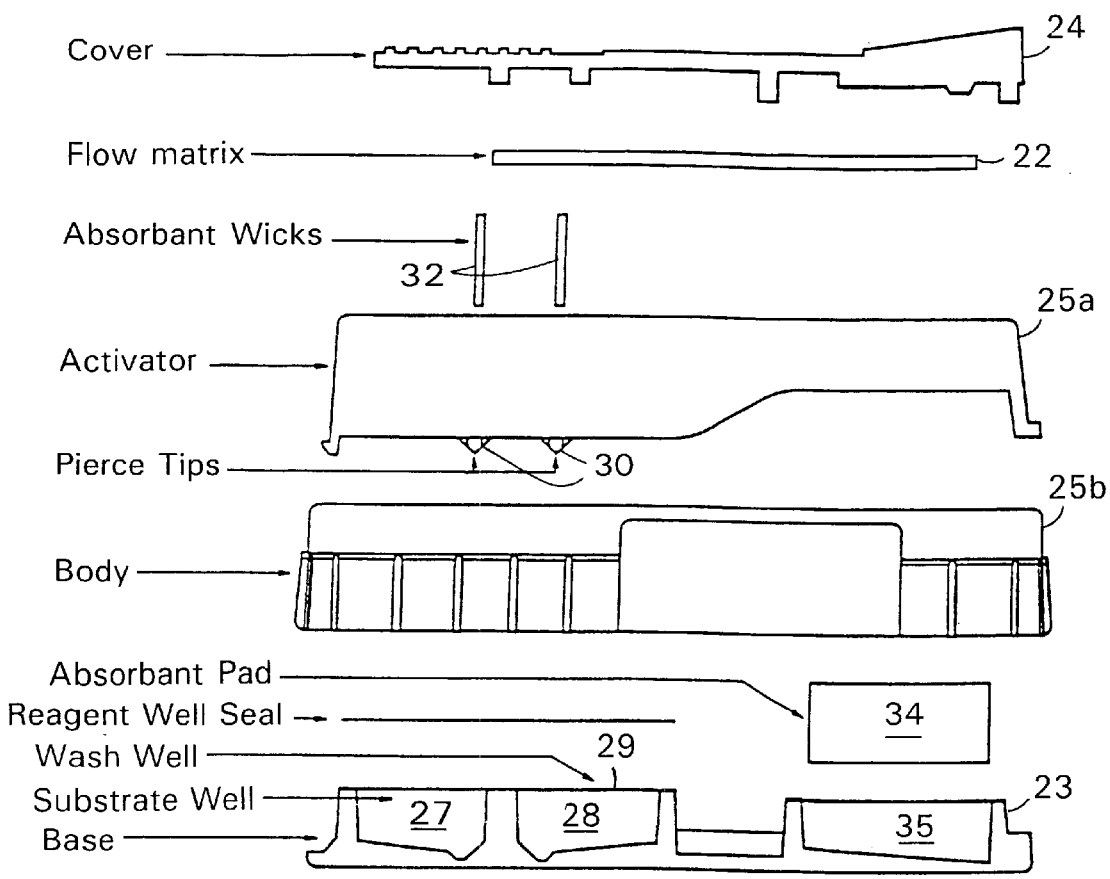
FIG. 2 is an exploded view of a single-use assay device for detecting FIV.
Figure 3:
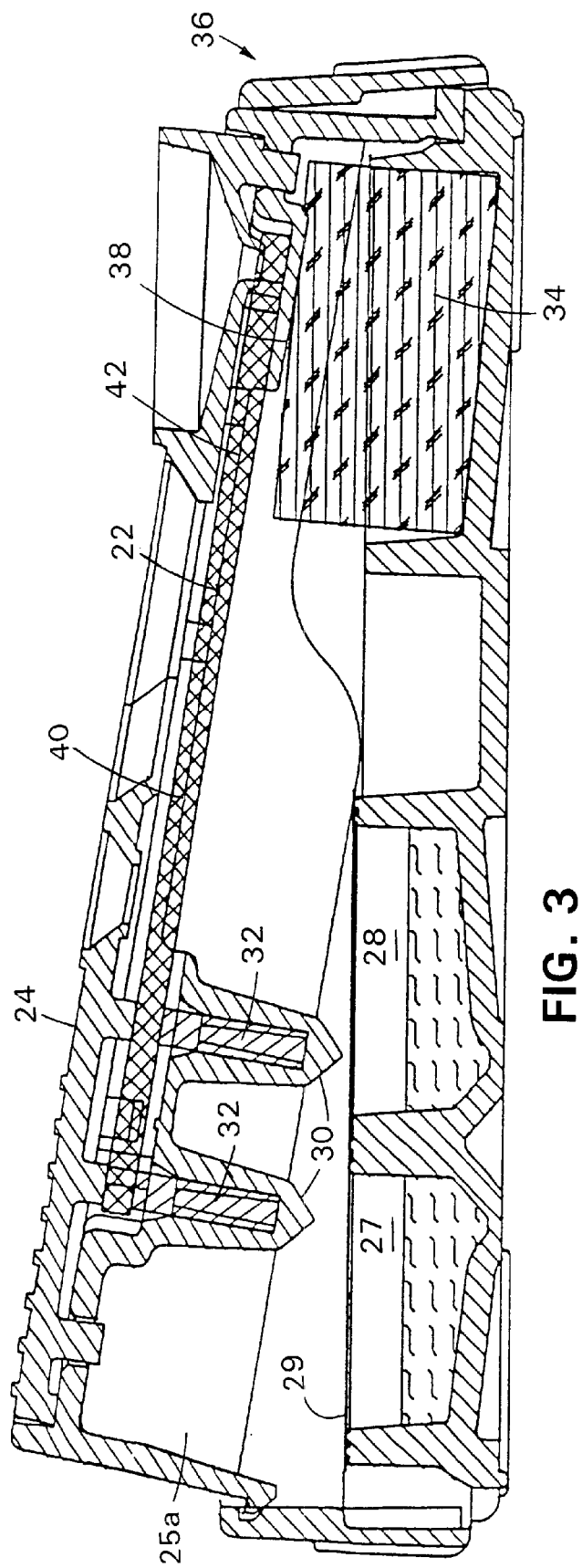
FIG. 3 is cross-section of the device of FIG. 2, assembled, before use.
Figure 4:
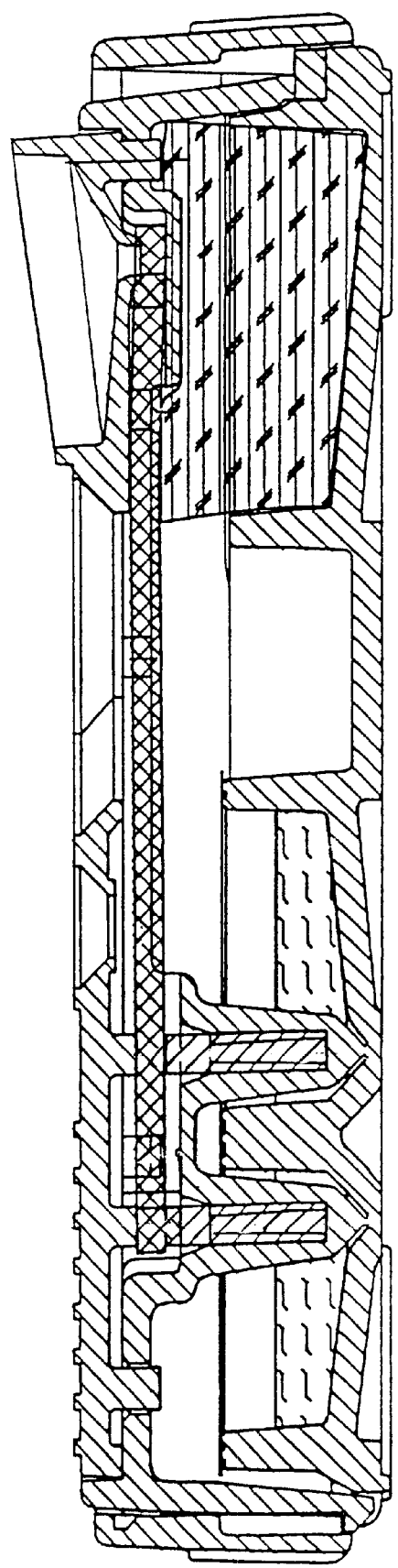
FIG. 4 is a cross-section of the device of FIG. 2 after use.

FIGS. 2–4 depict an exemplary single use device for performing a FIV assay. In FIG. 2, the device includes a bibulous flow matrix 22 held between a base 23 and a cover 24. An activator 25a and body 25b surround the flow matrix 22. Two reagent wells (an enzyme substrate well 27 and a wash well 28 are positioned in the base and covered by a well seal 29. The activator 25a includes two downwardly facing lances 30 which have absorbent wicks 32 at their core. An absorbent pad 34 is positioned in a recess 35 in the base.

In FIG. 3, before use, cover 24 and activator 25a are angled upward from hinge 36. Wells 27 and 28 are filled and covered. Sample is introduced into the sample cup 38, and sample flows from right to left (in FIG. 3) along matrix 22. Detection reagent designed to bind to and permit detection of FIV antibodies in the sample may be mixed with the sample before it is applied to the flow matrix, or it may be pre-applied to the matrix (e.g. at 42), to be picked up by FIV antibodies as sample moves along the matrix. An analyte capture zone 40 includes the capture reagents described elsewhere in this application. The capture reagents are immobilized to the capture zone 40 according to standard techniques, e.g., as described in U.S. Pat. Nos. 5,726,010 and 5,726,013. FIV antibodies that react with the capture reagents bind to the capture reagents and are thereby kept in zone 40. After a time set to permit the sample to move through zone 40, the activator 25a is closed by pivoting it around hinge 36. Lances 30 pierce well seal 29, permitting the solution of enzyme substrate in well 27 and the wash solution in well 28 to move up through wicks 32 and onto matrix 22. At the same time, absorbent pad 34 is brought into contact with matrix 22 just upstream (to the right in the figure) of sample cup 38, causing flow in the matrix to reverse (moving from left to right). This flow washes unbound material from zone 40, and brings enzyme substrate into contact with the conjugated enzyme of the capture reagents, causing a detectable (e.g. color-generating) reaction at zone 40 indicative of the presence of FIV antibody in the sample.

Other ELISA formats (e.g., microplate ELISA) can also be used. The results from ELISA experiments can be confirmed by Western blot analysis.

Capture reagents are attached to a phase immiscible with the test sample. For instance, the capture reagents are immobilized onto a solid phase. The solid phase can be in any form (e.g., a particle, a microplate well, or a strip), and can have, e.g., a unitary (planary or curved) surface or a porous structure. Materials useful as a solid support include, but are not limited to, glass, gels, paper, cellulose, nylon, polystyrene, and latex. The capture reagents can also be covalently linked to a water-immiscible solvent that can form an emulsion with the test sample to allow the contact between the capture reagents and the target antibodies.

Polypeptides serving as capture reagents can be attached to the solid surface by any of a number of standard methods, including direct adsorption or chemical coupling to reactive groups on the surface. For example, a solid surface can be derivatized to generate active amine groups; then an amine- and sulfhydryl-reactive heterobifunctional crosslinker (e.g., succinimidyl-4-(N-maleimidomethyl)cyclohexane-1-carboxylate ("SMCC") or other DOUBLE-AGENT™ crosslinkers available from Pierce, Rockford, Ill., or equivalent reagents from other vendors) is used to link a free cysteine group in the polypeptide to the amine group on the solid surface. Alternatively, homobifunctional crosslinkers also available from Pierce or other vendors can be used.

The capture polypeptides can contain an immunogenic fragment of p55 or gp130. To identify such immunogenic fragments, one can digest p55 or gp130 (or their natural cleavage products, e.g., p24 or gp40) with a peptidase or CNBR, and purify the immunogenic cleaved peptides by their ability to bind to an affinity column containing an anti-p55 or anti-gp130 antibody. Anti-p55 and anti-gp130 antibodies can be generated by well known methods. See, e.g., U.S. Pat. Nos. 5,177,014 and 5,219,725; Lombardi et al., AIDS Res Hum Retroviruses 9:141–146, 1993; and Lombardi et al., J Gen Virol 76(Pt 8):1893–1899, 1995.

Useful immunogenic fragments of gp130 include any of the four gp40 peptides shown at column 3 of U.S. Pat. No. 5,591,572. It can also be a segment of any one of these four gp40 peptide sequences that contains the core residues CNQNQFFC (SEQ ID NO:3). Such peptides contain an internal disulfide loop that maintains the immunogenic conformation of the corresponding region in native gp40. An exemplary gp40 capture reagent is a peptide (i.e., IRG2) consisting of amino acid residues CELGCNQNQFFCK (SEQ ID NO:2). This peptide has an internal disulfide bond formed by residues 5 and 12 during chemical synthesis. The cysteine residue at the amino terminal is not part of the corresponding native IDP, but is introduced to enable conjugation. For instance, the peptide can be linked via this cysteine to, e.g., bovine serum albumin ("BSA"), which can in turn be covalently attached or adsorbed to a solid surface. The carboxy terminus of IRG2 is optionally amidated to mimic the natural state of the carboxy terminus of IRG2.

The capture polypeptides can additionally contain an artificial epitope tag such as FLAG™ to facilitate purification and identification of the polypeptides. Of course, it is preferred that this epitope tag is not normally encountered by felines so that it does not cause cross-reactivity in the immunoassay. Protein tags such as β-galactosidase can be used as well (see, e.g., Mermer et al., Veterinary Immunology and Immunopathology 35:133–141, 1992).

Antibodies bound to the capture reagents on a solid support can be detected by an antibody-binding detection composition. This composition may include detection polypeptides that contain immunogenic sequences of p55 or gp130. For instance, disrupted FIV spiked with an immunogenic fragment of gp130 can be used as a detection composition. These antigens are linked to a detectable moiety such as a radionuclide (e.g., $^{125}I$ and $^{35}S$), a fluorophore (e.g., fluorescein, phycoerythrin, Texas Red, or Allophycocyanin), or an enzyme that catalyzes a colorimetric or chemiluminescence reaction (e.g. horseradish peroxidase and alkaline phosphatase). In one embodiment, the test sample is contacted with the labeled antigens while or prior to being applied to a solid phase. Alternatively, the labeled antigens are applied to the solid surface after the target antibody is bound. In any event, a complex will be formed on the solid surface by the target antibody, the labeled antigen, and the immobilized antigen. After unbound labeled antigens are washed away, signal generated from the solid surface is determined as an indication of the presence of bound antibody.

Polypeptides used as capture or detection reagents can be from natural FIV, or obtained by e.g., recombinant techniques or chemical synthesis. Nucleic acid constructs for expressing such polypeptides can be prepared by standard techniques such as polymerase chain reaction based on identified FIV nucleic acid sequences, e.g., the FIV genomic sequence disclosed in Talbott et al., Proc. Natl. Acad. Sci. USA 86:5743–5747, 1989.

The following example is meant to illustrate the methods and materials of the present invention. Suitable modifications and adaptations of the described conditions and parameters are within the spirit and scope of the present invention.

EXAMPLE

Screening of FIV Antibodies

Materials and Methods

Disrupted FIV antigens

The Crandall feline kidney (CRFK) cell line was used to propagate the Petaluma strain of FIV (O'Connor et al., J. Clin. Microbiol. 27:474–479,1989). Purified FIV was disrupted using a detergent (e.g., SDS or NP-40) and heat. Residual detergent was removed using BIO-BEADS prior to conjugation (Bio-Rad Labs, Richmond, Calif.).

Recombinant p24

The gene for p24 was amplified by the polymerase chain reaction ("PCR") from lysates of FIV Petaluma-infected CRFK cells. Primers were based on the published sequence (Talbott et al., Proc. Natl. Acad. Sci. USA 86:5743–5747, 1989). PCR products were cloned into pUC19, and inserts with verified DNA sequence were transferred to the appropriate pEX vector (Boehringer-Mannheim, Indianapolis, Ind.) to allow for synthesis of a β-galactosidase-p24 fusion protein (i.e., EXP24) in *E. coli* N48 30-1 (Boehringer-Mannheim). Expression of the proteins was induced by incubation of 42° C. for 2 hours.

The β-galactosidase fusion protein was purified from bacterial lysates as insoluble inclusion bodies by sonication and centrifugation as described previously (Hoppe et al., Biochemistry 28:2956–2960, 1989; Wingender et al., J. Biol. Chem. 264:4367–4373, 1989). Purity was assessed after Coomassie blue staining of SDS polyacrylamide gels by inspection or densitometry after PhastSystem (Pharmacia, Piccataway, N.J.) electrophoresis.

ELISA

ELISA analysis was performed by substitution of the recombinant antigens for the solid-phase whole virus antigen in the PETCHEK and SNAP assays (IDEXX Laboratories; see also Mermer et al., supra).

Capture Composition

The capture composition in the ELISA assays contained IRG2 and EXP24, where IRG2 was conjugated to BSA via SMCC. BSA-IRG2 and EXP24 were immobilized by passive adsorption onto a polystyrene solid surface at 2 μg/ml and 5 μg/ml, respectively.

Detection Composition

IRG2 was conjugated to horseradish peroxidase via SMCC. Disrupted native FIV was coupled to horseradish peroxidase via periodate chemistry. The mixture of the two conjugates at an approximate molar ratio of 1:1 were used as detection reagent.

Results

To test whether the BSA-IRG2/EXP24 capture composition can specifically detect antibody to gp40, a microplate ELISA was performed. Briefly, the inner walls of microwells in a microplate were coated with the capture composition. Fetal bovine serum ("FBS") containing various concentrations of an anti-gp40 mAb, i.e., mAb 2F11 or mAb 1C9, was then added to the wells. FBS containing an mAb to p27 of feline leukemia virus (mAb A2; see Lutz et al., J. Immunol. Meths. 56:209–220, 1983) was used as a negative control. IRG2 conjugated to horseradish peroxidase was used to detect anti-gp40 antibody that had bound to the wells. The results shown in Table 1 demonstrate that the p24/gp40 microplate ELISA can specifically detect anti-gp40 antibodies.

TABLE 1

| [mAb] | A2 | 2F11 | 1C9 |
|---|---|---|---|
| 100 μg/ml | 0.038 | 0.465 | 1.291 |
| 50 μg/ml | 0.062 | 0.415 | 1.421 |
| 10 μg/ml | 0.039 | 0.159 | 2.617 |
| 5 μg/ml | n/d* | 0.094 | 1.726 |
| 0 μg/ml | 0.044 | 0.044 | 0.044 |

*not determined.

Samples from 509 U.S. felines at risk for FIV infection were then screened for antibodies to p24 or to gp40. To detect antibodies to p24, PETCHEK (Mermer et al., supra) and SNAP, both of which are kits commercially available from IDEXX Laboratories (Westbrook, Me.), were used. To detect antibodies to gp40, WITNESS, a kit commercially available from Synbiotics Corporation (San Diego, Calif.), was used. A combination of the results obtained from both types of tests showed a prevalence of 13.8% (70/509) FIV-positive samples.

Of these 70 FIV-positive samples, 4 of them (5.7%) reacted only with p24 or gp40 antigens in these commercial tests. One sample was positive only in p24-based tests, while three other samples were positive only in gp40-based tests.

These discrepant samples gave positive results in ELISA, SNAP™, and Western blot analysis that detect both p24 and gp40 antibodies. This discovery demonstrates that detection of both p24- and gp40-directed antibodies is important for definitive results in FIV diagnostic tests.

Notably, the 439 samples that were negative in the PETCHEK assay were also negative on the SNAP assay that detects both p24 and gp40 antibodies. Thus, without wishing to bind ourselves to a specific theory (which is not necessary to practice the invention), we propose that the use of the two markers is particularly important in that each marker indicates some samples that the other marker misses, without a corresponding loss of selectivity, i.e., without a significant increase in false positive results.

Deposit

Under the terms of the Budapest Treaty on the International Recognition of the Deposit of Microorganisms for the Purpose of Patent Procedure, the deposits of hybridomas 3H9, 1C9, 2H4 and 3H8 have been made with the American Type Culture Collection (ATCC) of Rockville, Md., USA, where the deposits were given Accession Number HB12528, HB12529, HB12530, and HB12531, respectively.

Applicants' assignee, Idexx Laboratories, Inc., represents that the ATCC is a depository affording permanence of the deposits and ready accessibility thereto by the public if a patent is granted. All restrictions on the availability to the public of the materials so deposited will be irrevocably removed upon the granting of the patent. The materials will be available during the pendency of the patent application to one determined by the Commissioner to be entitled thereto under 37 CFR 1.14 and 35 U.S.C. §122. The deposited materials will be maintained with all the care necessary to keep it viable and uncontaminated for a period of at least five years after the most recent request for the furnishing of a sample of the deposited materials, and in any case, for a period of at least thirty (30) years after the date of deposit or for the enforceable life of the patent, whichever period is longer. Applicants' assignee acknowledges its duty to replace the deposits should the depository be unable to furnish a sample when requested due to the condition of the deposits.

OTHER EMBODIMENTS

It is to be understood that while the invention has been described in conjunction with the detailed description thereof, the foregoing description is intended to illustrate and not limit the scope of the invention, which is defined by the scope of the appended claims. For example, polypeptides used to capture p24 and gp40 respectively can be immobilized in separate regions of a solid surface, where the detection of bound antibody in either region indicates that the feline donor of the test sample is infected with FIV.

Other aspects, advantages, and modifications are within the scope of the following claims.

What is claimed is:

1. A method of determining whether a feline is infected with feline immunodeficiency virus (FIV), the method comprising providing a bodily sample of the feline, contacting the sample with an antibody-binding capture composition that comprises (i) a first purified capture polypeptide said polypeptide being an immunogenic fragment of FIV gag precursor p55, and (ii) a second purified capture polypeptide consisting essentially of an immunogenic fragment of FIV env precursor gp130, and using a detecting composition to detect the reaction of antibodies in the sample with the capture composition, wherein the occurrence of the reaction indicates that the feline is infected with FIV, said detection composition comprising a first detection polypeptide consisting essentially of an immunogenic fragment of FIV gag precursor p55 and a second detection polypeptide said polypeptide being an immunogenic fragment of FIV env precursor gp130, the first and second detection polypeptides being labeled with a detectable moiety.

2. The method of claim 1, wherein the binding composition is attached to a phase that is immiscible with the sample.

3. The method of claim 2, wherein the phase is a solid phase.

4. The method of claim 1, wherein the first capture polypeptide comprises p24.

5. The method of claim 1, wherein the first capture polypeptide comprises p15.

6. The method of claim 1, wherein the first capture polypeptide comprises p10.

7. The method of claim 1 or 4, wherein the second capture polypeptide comprises a cysteine loop of gp40.

8. The method of claim 7, wherein the second capture polypeptide has the sequence ELGCNQNQFFCK (SEQ ID NO:1) or CELGCNQNQFFCK (SEQ ID NO:2).

9. The method of claim 1 or 4, wherein the second capture polypeptide comprises gp110.

10. The method of claim 1, wherein the second detection polypeptide comprises the sequence ELGCNQNQFFCK (SEQ ID NO:1) or CELGCNQNQFFCK (SEQ ID NO:2).

11. The method of claim 1, wherein the detection composition comprises disrupted FIV and a peptide whose sequence is SEQ ID NO:1 or 2, both of the disrupted FIV and the peptide being labeled with a detectable moiety.

12. The method of claim 1 or 11, wherein the detectable moiety is an enzyme that catalyzes a detectable reaction.

13. The method of claim 1, wherein the detectable moiety is colloidal gold, a radionuclide or a fluorophore.

14. A device for performing an assay that determines whether a feline is infected with feline immunodeficiency virus (FIV), the device comprising an antibody-binding capture composition comprising (i) a first purified capture polypeptide said polypeptide being an immunogenic fragment of FIV gag precursor p55, and (ii) a second purified capture polypeptide said polypeptide being an immunogenic fragment of FIV env precursor gp130, and an antibody-binding detection composition for detecting the presence of antibodies bound to the capture composition, said detection composition comprising a first detection polypeptide, said polypeptide being an immunogenic fragment of FIV gag precursor p55, or a second detection polypeptide, said polypeptide being an immunogenic fragment of FIV env precursor gp130, or both, the first and second detection polypeptides in the detection composition being labeled with a detectable moiety.

15. The device of claim 14, wherein the binding composition is attached to a phase that is immiscible with the sample.

16. The device of claim 15, wherein the phase is a solid phase.

17. The device of claim 14, wherein the first capture polypeptide comprises p24.

18. The device of claim 14, wherein the first capture polypeptide comprises p15.

19. The device of claim 14, wherein the first capture polypeptide comprises p10.

20. The device of claim 14 or 17, wherein the second capture polypeptide comprises a cysteine loop of FIV gp40.

21. The device of claim 20, wherein the second capture polypeptide has the sequence ELGCNQNQFFCK (SEQ ID NO:1) or CELGCNQNQFFCK (SEQ ID NO:2).

22. The device of claim 14, wherein the second detection polypeptide comprises the sequence ELGCNQNQFFCK (SEQ ID NO:1) or CELGCNQNQFFCK (SEQ ID NO:2).

23. The device of claim 14, wherein the detection composition comprises disrupted FIV and a peptide whose sequence is SEQ ID NO:1 or 2, both of the disrupted FIV and the peptide being labeled with a detectable moiety.

24. The device of claim 14, wherein the detectable moiety is an enzyme that catalyzes a detectable reaction.

25. The device of claim 23, wherein the detectable moiety is an enzyme that catalyzes a detectable reaction.

26. The device of claim 14, wherein the detectable moiety is colloidal gold, a radionuclide or a fluorophore.

27. The device of claim 14, wherein the detection composition is held in a container.

28. A method of determining whether a feline is infected with feline immunodeficiency virus (FIV), the method comprising providing a bodily sample of the feline, contacting the sample with an antibody-binding capture composition that comprises (i) a first purified capture polypeptide said polypeptide being an immunogenic fragment of FIV gag precursor p55, and (ii) a second purified capture polypeptide said polypeptide being an immunogenic fragment of FIV env precursor gp130, and using a detecting composition to detect the reaction of antibodies in the sample with the capture composition, wherein occurrence of the reaction indicates that with FIV.

* * * * *

SEQUENCE LISTING

<160> NUMBER OF SEQ ID NOS: 3

<210> SEQ ID NO 1
<211> LENGTH: 12
<212> TYPE: PRT
<213> ORGANISM: Feline immunodeficiency virus

<400> SEQUENCE: 1

Glu Leu Gly Cys Asn Gln Asn Gln Phe Phe Cys Lys
1               5                   10

<210> SEQ ID NO 2
<211> LENGTH: 13
<212> TYPE: PRT
<213> ORGANISM: Feline immunodeficiency virus

<400> SEQUENCE: 2

Cys Glu Leu Gly Cys Asn Gln Asn Gln Phe Phe Cys Lys
1               5                   10

<210> SEQ ID NO 3
<211> LENGTH: 8
<212> TYPE: PRT
<213> ORGANISM: Feline immunodeficiency virus

<400> SEQUENCE: 3

Cys Asn Gln Asn Gln Phe Phe Cys
1               5